(12) United States Patent
Marienhagen et al.

(10) Patent No.: US 8,158,390 B2
(45) Date of Patent: Apr. 17, 2012

(54) METHOD FOR THE FERMENTATIVE PRODUCTION OF L-VALINE AND SUITABLE MICROORGANISM

(75) Inventors: Jan Marienhagen, Jülich (DE); Lothar Eggeling, Jülich (DE); Hermann Sahm, Jülich (DE)

(73) Assignee: Forschungszentrum Julich GmbH, Julich (DE)

( * ) Notice: Subject to any disclaimer, the term of this patent is extended or adjusted under 35 U.S.C. 154(b) by 1004 days.

(21) Appl. No.: 11/663,984

(22) PCT Filed: Aug. 19, 2005

(86) PCT No.: PCT/DE2005/001465
§ 371 (c)(1),
(2), (4) Date: Mar. 27, 2007

(87) PCT Pub. No.: WO2006/034667
PCT Pub. Date: Apr. 6, 2006

(65) Prior Publication Data
US 2008/0153139 A1 Jun. 26, 2008

(30) Foreign Application Priority Data
Sep. 28, 2004 (DE) .......... 10 2004 046 933

(51) Int. Cl.
| | |
|---|---|
| C12P 13/08 | (2006.01) |
| C12P 21/06 | (2006.01) |
| C12N 9/00 | (2006.01) |
| C12N 9/10 | (2006.01) |
| C12N 15/70 | (2006.01) |
| C07H 21/04 | (2006.01) |

(52) U.S. Cl. ....... 435/115; 435/69.1; 435/183; 435/193; 435/252.32; 435/320.1; 536/23.2

(58) Field of Classification Search .......... None
See application file for complete search history.

(56) References Cited

U.S. PATENT DOCUMENTS 7,202,060 B2 * 4/2007 Ikeda et al. .......... 435/106

FOREIGN PATENT DOCUMENTS

EP 1 275 729 A1 3/2001

OTHER PUBLICATIONS

Whisstock et al. Quaterly Reviews of Biophysics, 2003, "Prediction of protein function from protein sequence and structure", 36(3): 307-340.*
Radmacher et al. Appl Environ Microbiol. May 2002;68(5):2246-50. Linking central metabolism with increased pathway flux: L-valine accumulation by *Corynebacterium glutamicum*.*
Steger et al. LcoP, an osmoregulated betaine/ectoine uptake system from *Corynebacterium glutamicum*. FEBS Lett. Aug. 27, 2004;573(1-3):155-60.*
NCBI Sequence Viewer Record # NC 003450 now replaced by 58036263 Nakagawa, S. "Complete genomic sequence of *Corynebacterium glutamicum* ATCC 13032" National Center for Biotechnology (Sep. 23, 2002).
Marienhagen, J.; Kennerknecht, N.; Sahm, H.; & Eggeling, L; Functional Analysis of All Aminotransferase Proteins Inferred from the Genome Sequence of *Corynebacterium glutamicum; Journal of Bacteriology*, Nov. 2005; p. 7639-7646.
Wang, M-D.; Buckley, L.; & Berg, C.M.; Cloning of Genes That Suppress an *Escherichia coli* K-12 Alanine Auxotroph When Present in Multicopy Plasmids; *Journal of Bacteriology*; Dec. 1987; p. 5610-5614.
Leyval, D.; Uy, D.; Delaunay, S.; Goergen, J.L.; & Engasser, J.M.; Characterisation of the enzyme activities involved in the valine biosynthetic pathway in a valine-producing strain of *Corynebacterium glutamicum*; *Journal of Biotechnology*; p. 241-252.
Re.Jap.Pat.Appl. 2007-532758; *Corynebacterium glutamicum* ATCC 13032, complete genome; Sep. 2002.

* cited by examiner

*Primary Examiner* — Anand Desai
*Assistant Examiner* — Iqbal H Chowdhury
(74) *Attorney, Agent, or Firm* — Jonathan Myers; Andrew Wilford

(57) ABSTRACT

The invention relates to a method for producing L-valine and to a suitable microorganism. The inventive method is characterized by preferably enhancing the transaminase C activity of a *coryneform bacterium*, especially *Corynebacterium glutamicum*. The organisms so modified have a yield in L-valine which is 35.8% higher than that of non-modified organisms.

7 Claims, 1 Drawing Sheet

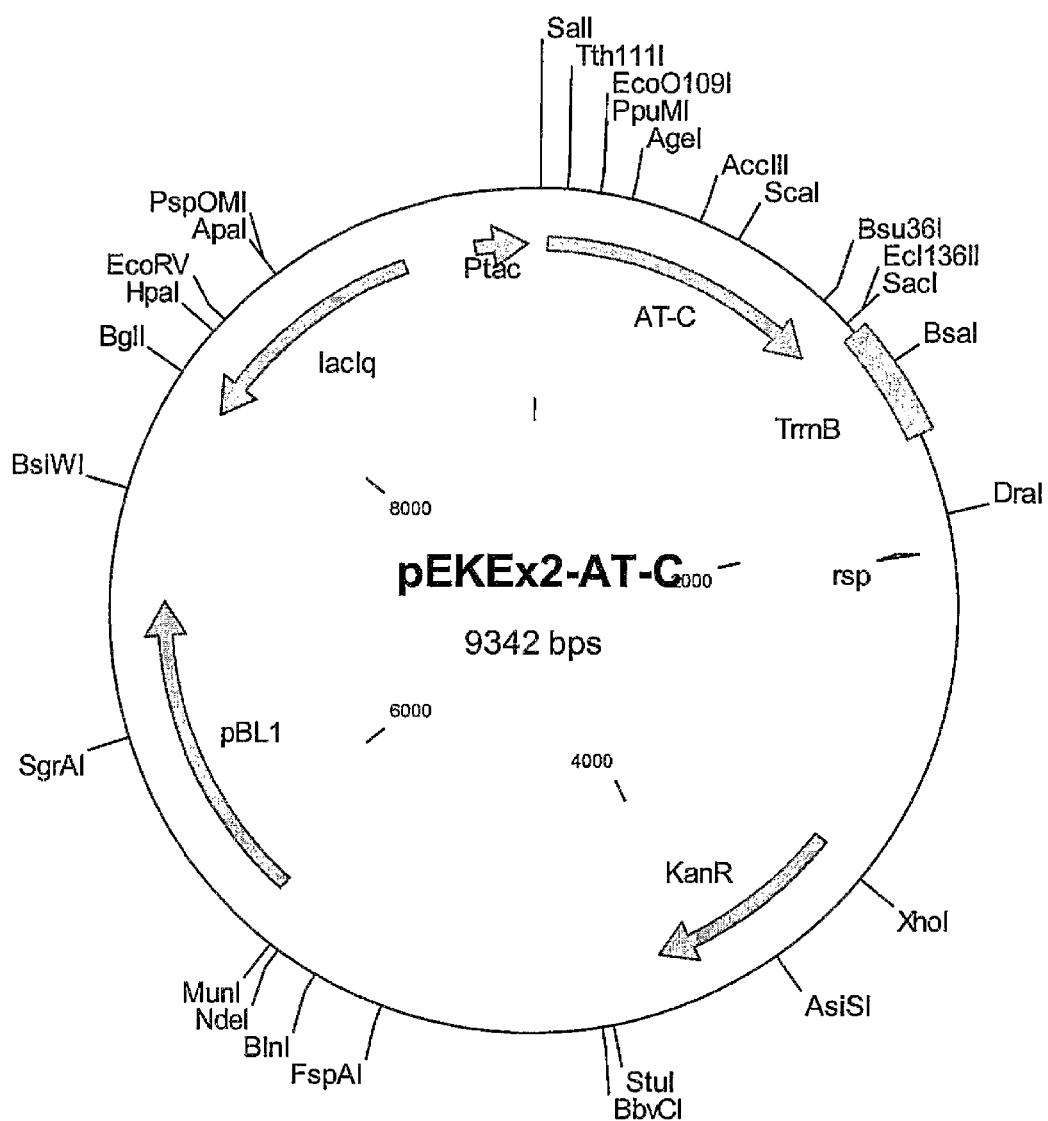

METHOD FOR THE FERMENTATIVE PRODUCTION OF L-VALINE AND SUITABLE MICROORGANISM

CROSS REFERENCE TO RELATED APPLICATIONS

This application is the US national phase of PCT application PCT/DE2005/001465, filed 19 Aug. 2005, published 6 Apr. 2006 as WO 2006/034667, and claiming the priority of German patent application 102004046933.4 itself filed 28 Sep. 2004.

FIELD OF THE INVENTION

The invention relates to a method for the production of L-valine as well as a suitable microorganism.

BACKGROUND OF THE INVENTION

The amino acid L-valine is used in human medicine, in the pharmaceutical industry, in the food industry as well as in pet food.

It is known that amino acids are produced from the fermentation of strains of coryneform bacteria, particularly *corynebacterium glutamicum*. Due to their great importance, the manufacturing processes are continually improved. Manufacturing improvements can relate to fermentation measures, such as agitation and supply with oxygen for example, or to the composition of the nutrient solutions, such as the glucose concentration during fermentation, or the processing into the product form, for example through ion exchange chromatography or the intrinsic performance characteristics of the microorganism itself.

Methods of mutagenesis, selection, and mutant selection are used to improve the performance characteristics of these microorganisms. By doing so, strains are obtained that are resistant to anti-metabolites or that are auxotrophic for regulatory significant metabolites and produce L-amino acids. Such a *corynebacterium* strain is described, for example in the U.S. Pat. No. 5,521,074, which strain is resistant to L-valine and sensitive to fluoropyruvic acid. Furthermore, it is described in EP 0287123 that *corynebacteria* with resistance to mycophenolic acids can be used advantageously for L-valine production. From EP 0519113 A1 and U.S. Pat. No. 5,658,766 it is also known that the mutants with mutated valyl-tRNA synthetase in combination with further mutations can be used for L-valine production. In addition, WO 001996006926 A1 describes a process for the production of L-valine, wherein a microorganism is used that requires the vitamin lipoic acid for growth and has a defect in the ATPase.

Recombinant DNA technology is additionally used for improving the intrinsic characteristics of L-amino acids-producing strains of *corynebacterium*. The documents EP 1155139B1 and EP 0356739 B1, for example, describe that the enhancement of the expression of the biosynthesis genes ilvBN, ilvC, and ilvD is advantageously used for the production of L-valine. Furthermore, it is known from EP 1155139 B1 that for L-valine production the weakening or elimination of the threonine dehydratase gene ilvA and/or of genes of the pantothenate synthesis can be used.

OBJECTS OF THE INVENTION

It is the object of the invention to provide a method and a suitable microorganism for the improved fermentative production of L-valine.

It is a further object of the invention to provide a method for the fermentative production of L-valine using coryneform bacteria, in which transaminase C is modified and/or transaminase C expression is enhanced.

SUMMARY OF THE INVENTION

According to the invention a method is disclosed for the fermentative production of L-valine wherein Transaminase C activity in a microorganism is increased.

It was found that the coryneform bacteria produce L-valine in an improved manner after enhancement of the genes coding for transaminase C. With the method according to the invention, it is now possible to produce L-valine in a yield that is 35.8% higher than with a strain that is not modified according to the invention.

Following the description of the invention.

According to the invention, the transaminase C activity is enhanced in a microorganism that produces the amino acid L-valine.

The strains used preferably produce L-valine already before enhancement of the transaminase C gene.

As microorganism, a *coryneform bacterium* is preferably used.

Particularly preferred are *corynebacterium glutamicum, corynebacterium acetoglutamicum, corynebacterium thermoanimogenes, brevibacterium flavum, brevibacterium lactofermentum, brevibacterium divaricatum*.

Particularly suited strains of the category *corynebacterium*, particularly of the type *corynebacterium glutaminum*, are for example the known wild-type strains

*Corynebacterium glutaminum* ATCC13032
*Corynebacterium acetoglutamicum* ATCC15806.
*Corynebacterium acetoacidophilum* ATCC13870
*Corynebacterium thermoaminogenes* FERN BP-1539
*Brevibacterium flavum* ATCC14067
*Brevibacterium lactofermentum* ATCC13869 and
*Brevibacterium divaicatum* ATCC14020 and mutants, or strains produced from these and producing an excess of L-amino acid.

The microorganisms that are the object of the present invention can produce L-valine for example from glucose, saccharose, lactose, fructose, maltose, molasses, starches, cellulose, or from glycerin and ethanol. They are representatives of *coryneform bacteria*, particularly the type *corynebacterium*. From the category *corynebacterium*, particularly the type *corynebacterium glutamicum* should be mentioned, which is known among experts for its ability to produce L-amino acids.

In terms of the invention, the term "enhancement" is interpreted as the increase of intracellular transaminase C activity, e.g. through following actions:
Increase of the gene expression through at least one step from the group comprising:
Modifications of the signal structures of the gene expression, such as through modification of the
repressor genes,
activator genes,
operators,
promoters;
attenuators,
ribosome binding sites,
start codon,
terminators
Introduction of a stronger promoter, such as a tac-promoter, or an IPTG-inducible promoter for example.

Increase of the gene copy count, e.g. by introduction of vectors like plasmides, increase of the endogenous gene copy count, meaning the introduction of further genes coding for transaminase C or alleles thereof into the chromosomal genome.

Furthermore, an enhancement of the transaminase C activity can be provoked through the following measures:

Increase of the m-RNA-stability, for example through mutation of terminal positions that control the termination of transcription.

For example, through stability of the m-RNA of the transaminase C gene an improved product creation can be achieved in that the stability is positively influenced by additional and/or modified sequences on the 5'-end or the 3'-end of the gene. General examples for this are genes from *bacillus subtilis* (Microbiology 2001, 147:1331-41) or yeast (Trends Biotechnol. 1994, 12:444-9).

Use of a gene or allele that codes for a corresponding enzyme with increased activity.

The increase of the intracellular activity of one or more enzymes (proteins) within a microorganism, which enzymes are coded for by the corresponding DNA, can be enhanced by the use of a strong promoter or a gene, or as the case may be, by an allele that codes for a corresponding enzyme with increased activity, or overexpresses the corresponding gene (protein) and, as the case may be, combines these measures.

The introduction of a stronger promoter, such as the tac-promoter (Amann et al (Gene 1988 69:301-15)) for example, or promoters from the group of promoters described in Patek et al (Microbiology 1996 142:1297), is preferred. Examples can be found in WO 96/15246 or in Boyd and Murphy (Journal of Bacteriology 170: 5949 (1998)), in Voskuil and Chambliss (Nucleic Acids Research 26: 3548 (1998), in Jensen and Hammer (Biotechnology and Bioengineering 58: 191 (1998)), in Pátek et al (Microbiology 142: 1297 (1996)), Knippers ("Molekulare Genetic [Molecular Genetics]", $6^{th}$ edition, Georg Thieme publishing house, Stuttgart, Germany 1995), or also at Winnacker ("Gene und Klone [Genes and Clones]", VCH publishing company, Weinheim, Germany, 1990).

The natural nucleotide sequence of the transaminase C gene is inevitably known as a result of the creation of the complete genome sequence of *C. Glutamicum* (Kalinowski et al, 2003, J. Biotechnol., 104:5-25; Ikeda M, and Nakagawa S. 2003 Appl. Microbiol. Biotechnol. 62:99-109), however without knowledge of the association of an open reading frame for transaminase C. It is also known that *c. Glutamicum* (Leyval et al 2003. J. Biotechnol. 104:241-52) as well as for example *E. coli* have transaminase C activity (Wang et al 1987, J. Bacteriol. 169:4228-4234). The open reading frame as subsequently described and identified in the example, which codes for transaminase C, bears the number NCgl2510 and has SEQ ID NO: 1 which encodes Transaminase C from *Coryneform Glutamicum* having SEQ ID NO: 2, and is stored in the publicly accessible database of the "National Institute of Health" (ncbi.nlm.nih.gov), the identical gene also being identified under Cg12599 in the publicly accessible "DNA Data bank of Japan" (gib.genes.nig.ac.jp).

The transaminase-C-gene described by these numbers is preferably used according to the invention. Furthermore, the allele of the transaminase C gene can be used, which for example results from the degeneration of the genetic code or from functionally neutral sense mutations or from the deletion or insertion of nucleotides.

In order to achieve an enhancement, either the expression of the transaminase C gene or the catalytic properties of the enzyme protein can be increased, or as the case may be enhanced. The catalytic property of the enzyme protein can also be modified in regard to its substrate specificity. If necessary, both measures can be combined.

The enhancement of gene expression can take place through suitable culture management, or through genetic modifications (mutation) of the signal structures of the gene expression. The signal structures of the gene expression are, for example, repressor genes, activator genes, operators, promoters, attenuators, ribosome binding sites, the start codon, and terminators. The person skilled in the art can find information hereunto e.g. in the patent application WO 96/15246, at Boyd and Murphy (J. Bacteriol. 1988.170: 5949), at Voskuil and Chambliss (Nucleic Acids. Res. 1998. 26: 3548), at Jensen and Hammer (Biotechnol. Bioeng. 1998 58: 191), at Patek et al. (Microbiology 1996. 142:1297), and in known textbooks for genetics and molecular biology, such as for example the textbook by Knippers ("Molekulare Gentechnik [Molecular Genetics]", $8^{th}$ edition, Georg Thieme publishing house, Stuttgart, Germany, 2001), or one by Winnacker ("Gene und Klone [Genes and Clones]", VCH Verlagsgesellschaft, Weinheim, Germany, 1990).

Mutations resulting in a modification of the catalytic properties of enzyme proteins, particularly in modified substrate specificity, are known from the state of the art. As an example, the works of Yano et al 1998 Proc Natl Acad Sci U S A. 95:5511-5, Oue S. et al J. Biol Chem. 1999, 274:2344-9, and Onuffer et al Protein Sci. 1995 4:1750-7 should be mentioned, in which the modification of the specificity of *aspartate aminotransferases* is revealed. Transitions, transversions, insertions, and deletions can be considered as mutations, as well as methods of directed evolution. Instructions for the production of such mutations and proteins are part of the state of the art and can be gathered from known textbooks (R. Knippers "Molekulare Genetik [Molecular Genetics]", $8^{th}$ edition, 2001 Georg Thieme publishing house, Stuttgart, Germany), or review articles (N. Pokala 2001, J. Struct. Biol. 134:269-81; A. Tramontano-2004, Angew. Chem. [Applied Chemistry] Int. Bd Engl. 43:3222-3; N. V. Dokholyan 2004, Proteins. 54:622-8; J. Pei 2003, Proc. Natl. Acad. Sci U S A. 100:11361-6; H. Lilie 2003, EMBO Rep. 4:346-51; R. Jaenicke Angew. Chem. [Applied Chemistry] Int. Ed. Engl. 42:140-2).

The expression of the genes or mutated genes preferably takes place according to conventional methods of increasing the copy count through the integration into suitable plasmids. Plasmids that are replicated in coryneform bacteria are suitable. Numerous known plasmid vectors, such as pz1 (Menkel et al, Applied and Environmental Microbiology (1989) 64:549-554), pEKEx1 (Eikmanns et al, Gene 102:93-98 (1991)), or pHS2-1 (Sonnen et al, Gene 107:69-74 (1991)) for example, are based on the cryptic plasmids pHM1519, pBL1 or bGA1. Other plasmid-vectors, as for example those that are based on pCG4 (U.S. Pat. No. 4,489,160) or pNG2 (Serwold-Davis et al, FEMS Microbiology Letters 66, 119-124 (1990)) or pAG1 (U.S. Pat. No. 5,158,891) can also be used (O. Kirchner 2003, J. Biotechnol. 104:287-99). Vectors with adjustable expression, such as for example pEKEx2 (B. Eikmanns, 1991 Gene 102:93-8; O. Kirchner 2003, J. Biotechnol. 104:287-99), can be used as well. The gene can also be expressed through integration in the chromosome in single copy (P. Vasicova 1999, J. Bacteriol. 181:6188-91), or multiple copies (D. Reinscheid 1994 Appl. Environ Microbiol 60:126-132).

The transformation of the desired strain with the vector in order to increase the copy count takes place by conjugation or electrophoration of the desired strain of *C. glutamicum*, for example. The method of conjugation is described by Schäfer et al (Applied and Environmental Microbiology (1994) 60:756-759), for example. Methods for transformation are described by Tauch et al (FEMS Microbiological Letters (1994) 123:343-347) for example.

This way, the transaminase C gene or its allele can be expressed or overexpressed in C. glutamicum.

Furthermore, it can be advantageous for the production of L-valine, in addition to increasing the transaminase C activity, to enhance one or more genes chosen from the group of
    the ilvBN gene coding for acetohydroxyacid synthase,
    the gene coding for isomer reductase,
    the ilvD gene coding for dehydratase
particularly to overexpress, or to enhance or overexpress alleles of these genes, in particular
    the ilvBN genes coding for feedback-resistant acetohydroxy acid synthase,
in order to further increase the production of L-valine.

Furthermore, it can be advantageous for the production of L-valine, in addition to increasing the transaminase C activity, to deactivate or reduce in their expression, or to mutate, one or more genes chosen from the group of
    the panBCD genes coding for pantothenate synthesis,
    the lipAB genes coding for lipoic acid synthesis,
    the aceE, aceF, 1pD genes coding for pyruvate dehydrogenase,
    the genes for the genes of the ATP synthase A subunit, ATP synthase B subunit, ATP synthase C subunit, ATP synthase alpha subunit, ATP synthase gamma subunit, ATP synthase subunit, ATP synthase epsilon subunit, ATP synthase delta subunit, in order to create-functionally weakened gene products, so the production of L-valine can be increased.

The microorganisms produced according to the invention can be cultivated continuously or discontinuously in a batch procedure (batch cultivation) or in the fed batch (feed procedure) or repeated fed batch procedure (repetitive feed procedure) for the purpose of valine production. A summary of known cultivation procedures is described in the textbook of Chmiel (Bioprozesstechnik 1. Einfuehrung in die Bioverfahrenstechnik [Bioprocess Technology 1$^{st}$ Introduction into Bio-procedure Technology] (Gustav Fischer Verlag, Stuttgart, 1991)), or in the textbook by Storhas (Bioreaktoren und periphere Einrichtungen [Bioreactors and Peripherals Devices] (Vieweg publishing house, Braunschweig/Wiesbaden (1994)).

The culture medium to be used must meet the requirements of the respective microorganisms. Descriptions of culture media of different microorganisms are included in the handbook "Manual of Methods for General Bacteriology" of the American Society for Bacteriology (Washington D.C., USA, 1981).

Possible carbon dioxide sources include sugar and carbohydrates, such as glucose, saccharose, lactose, fructose, maltose, molasses, starch and cellulose, oils and fats, such as soy oil, sunflower seed oil, peanut oil and coconut oil, fatty acids, such as palmitic acid, stearic acid and linoleic acid, alcohols such as glycerin and ethanol, as well as organic acids, such as acetic acid.

These substances can be used individually or as a mixture.

Possible nitrogen sources are organic, nitrogen-containing compounds like peptones, yeast extract, meat extract, malt extract, corn steep liquor, soybean flour and urea, or inorganic compounds like ammonium sulfate, ammonium chloride, ammonium phosphate, ammonium-carbonate, and ammonium nitrate. The nitrogen sources can be used individually or as a mixture.

As the phosphorus source, potassium dihydrogen phosphate or di-potassium hydrogen phosphate, or the corresponding sodium-containing salts can be used.

Furthermore, the culture medium should include salts of metals, such as magnesium sulfate, or ferric sulfate for example, which are necessary for growth. Lastly, essential growth substances, such as amino acids and vitamins can be used in addition to the above-mentioned substances. The ingredients mentioned above can be added to the culture in the form of a one-time mixture, or they can be added in a suitable manner during cultivation.

In order to control the pH level of the culture, basic compounds like sodium hydroxide, potassium hydroxide, ammonia, or acid compounds like phosphoric acid, or sulfuric acid can be used in an appropriate manner. To control foam development, de-foaming agents, such as fatty acid polyglycolester, can be used. In order to maintain the stability of the plasmids, selective substances, for example antibiotics, can be added to the medium. In order to maintain aerobic conditions, oxygen or oxygen-containing gas mixtures, for example air, can be introduced into the culture. The temperature of the culture is normally between 20° C. and 45° C., and preferably between 25° C. and 40° C. The culture is cultivated until a maximum of L-valine has formed. This goal is usually reached within 10 hours to 160 hours.

BRIEF DESCRIPTION OF THE DRAWING

The sole FIGURE in this case is a map of plasmid pEKEx2ATC, used for the transformation of the Corynebacterium glutamicum strain 13032ΔpanBC to overexpress Transaminase C from Corynebacterium glutamicum to catalyze the biosynthesis of L-valine from L-alanine and ketoisovalerate.

EXAMPLES

Example 1

Cloning of Transaminase C

With the aid of the PCR reaction, a DNA fragment comprising the transaminase C gene having SEQ ID NO: 1, was amplified. The following primer were used:

```
orf2841-for:
5'-ATGGTA (GGTCT) CAAATGTCTCTTATGAAGCCAAGCACTAG-3' orf2841-rev (SEQ ID NO: 3):
                                            (SEQ ID NO: 4)
5'-ATGGTA (GGTCT) CAGCGCTTTTTTTGATGAATTCTCCGATTTT
G-3'
```

The primers listed were synthesized by MWG Biotech, and the PCR reaction was carried out in accordance with standard protocols (Innis et al PCR Protocols. A. Guide to Methods and Applications. 1990. Academic Press). A DNA fragment of about 1.1 kb was amplified with the primers that fragment codes for transaminase C. The primers comprise additionally the interface of the restriction enzyme BsaI that are shown in the above nucleotide sequences in brackets.

The amplified DNA fragment of about 1.1 kb was identified in the 0.8% agarose gel and was isolated from the gel with existing methods (QIAquik Gel Extraction Kit, Quiagen, Hilden). The ligation of the fragment was carried out with the SureCloning Kit (Amersham, UK) into the expression vector pASK-IBA-3C (IBA, Goettingen). With this ligation approach, E. coli DH5 was transformed (Grant et al, 1990. Proceedings of the National Academy of Science of the United States of America USA, 87:4645-4649). The selection of plasmid-containing strains was done by plating the transformation mixture onto LB-plates containing 25 mg of chloramphenicol per liter.

After plasmid isolation, the resulting plasmids were characterized by restriction digest and gel electrophoresis analysis. The resulting plasmid was labeled as pASK-IBA-3Corf2841.

Example 2

Isolation of Transaminase C

E. coli EH5 with pASK-IBA-3Corf2841 was cultured at 30° C. in 100 ml LB with 25 mg of chloramphenicol per liter to an optical density of 0.5. Then 0.01 ml of an anhydrotetracycline solution was added that comprised 2 mg of anhydrotetracycline per milliliter of dimethylformamide. The culture was incubated for 3 more hours at 30° C. Afterward, the cells were harvested through centrifugation for 12 minutes at 4° C. and 5000 revolutions per minute. Then the cell pellet was resuspended in wash buffer (100 mm trihydroxymethylaminomethane, 1 mM ethylene diaminetetraacetic acid, pH8) and transferred to an Eppendorf reaction tube. The cell disruption occurred at 0° C. with an ultrasound disintegrator (Branson Sonifier W-250, Branson Sonic Power Company, Danbury, USA; acoustic irradiation time 10 min., pulse length 20%, acoustic irradiation intensity 2). After the ultrasound treatment, the cell debris was separated by centrifugation (30 min., 13000 Rpm, 4° C.) and the raw extract was obtained as supernatant.

For the isolation of the protein StrepTactin-Affinity Columns from the manufacturer IBA (IBA, Göttingen, Germany) were filled with 1 ml bed volume StrepTactin-sepharose. After equilibration of the columns with wash buffer from the manufacturer IBA, 1 ml of the raw extract was applied to the sepharose. After the passage of the extract, the affinity column was washed 5 times with 1 ml wash buffer. The elution of the transaminase-C protein was carried out with elution buffer, comprising 100 mM Tris, 1 mM EDTA, 2.5 mM desthiobiotin, pH 8. The elution fractions were aliquoted, frozen at −20° C., and used directly in the enzyme test.

Example 3

Activity Determination of Transaminase C

The reaction batch of the enzyme test comprised in a total volume of 1 ml: 0.2 ml 0.25 M Tris/HCl, pH 8, 0.005 ml transaminase-C protein, and 0.1 ml 2.5 mM pyridoxal phosphate, as well as 0.1 ml 40 mM ketoisocaproate and 0.1 ml 0.5 M L-alanine, or 0.1 ml 40 mM ketoisovalerate and 0.1 ml 0.5 M L-alanine, or 0.1 ml 40 mM ketoisocaproate and 0.1 ml 0.5 M L-glutamine, or 0.1 ml 40 mM ketoisocaproate and 0.1 ml 0.5 M L-alanine without transaminase-C protein. The enzyme test was carried out at 30° C. in a thermocycler 5436 from the company Eppendorf (Hamburg). The reaction was started by adding the protein. By adding 30 μl of a stop reagent (6.7%) (v/v) perchloric acid (70%), 40% (v/v) ethanol (95% (in water)) to each 50 μl of the test batch, the enzyme test was stopped. In order to prepare the samples for the verification of the formed aminoacids via reversed phase HPLC, 20 μl of a neutralizing buffer (20 mM Tris, 2.3 M dipotassium carbonate, pH 8) was added. The deposit precipitated as a result of the neutralization of perchloric acid was centrifuged off (13000 Rpm, 10 min) and the supernatant was used in different dilutions for the quantification via HPLC. This was carried out following automatic derivatization with o-phthaldialdehyde, as described (Hara et al 1985, Analytica Chimica Acta 172:167-173). As table 1 shows, the isolated protein having SEQ ID NO: 2 catalyses the L-alanine dependent amination from ketoisovalerate into L-valine.

TABLE 1

| Protein | Amino-donator | Amino-acceptor | Product | Spec. Activity |
|---|---|---|---|---|
| Transaminase C | L-Alanine | Ketoisocaproate | L-Leucine | 0.9 |
| Transaminase C | L-Alanine | Ketoisovalerate | L-Valine | 18.2 |
| Transaminase C | L-Alanine | Kethometylvalerate | L-Isoleucine | 3.7 |
| Transaminase C | L-Glutamine | Kethoisovalerate | L-Valine | 0.1 |
| Control | L-Alanine | Ketoisovalerate | L-Valine | 0.0 |

The specific activity (spec. activity) is shown in micromol of product per minute and milligram transaminase C protein.

Example 4

Overexpression of Transaminase C

With the aid of the PCR reaction, a DNA-fragment comprising the Transaminase C gene was amplified. The following primers were used:

Trans_c_for:
5'-CGGGATCCAAGGAGATATAGATATGTCTCTTATGAAGCCAAGCA-3'

Trans_c_rev (SEQ ID NO: 5):
(SEQ ID NO: 6)
5'-CGGGATCCCTATTTTTTGATGAATTCTCC-3'

The primers listed were synthesized by MWG Biotech, and the PCR reaction was carried out according to standard protocols (Innis et al PCR Protocols. A Guide to Methods and Applications. 1990. Academic Press.) A DNA fragment of approximately 1.1 kb was amplified with the primers that fragment codes transaminase C. The primers comprise additionally the interface of the restriction enzyme BamHI.

The amplified DNA-fragment of approximately 1.1 kb was identified in 0.8% agarose gel and isolated from the gel with existing methods (QIAquik Gel Extraction Kit, Quiagen, Hilden). The ligation of the fragment was carried out with the SureCloning Kit (Amersham, UK) into the expression vector pEKEx2 (Bikmanns et al 1991, Gene 102:93-8). With the ligation batch, E. coli DH5 was transformed (Grant et al, 1990. Proceedings of the National of Sciences of the United States of America USA, 87:4645-4649). The selection of plasmid-comprising strains took place by plating the transformation batch to LB plates with 25 mg per liter of kanamycin.

After the plasmid isolation, the resulting plasmids were characterized by restriction digest and gel electrophoresis analysis. The resulting plasmid was labeled pEKEx2ATC.

The plasmid pEKEx2ATC, as well as the starting plasmid pEKEx2 were used for the transformation of the 13032ΔpanBC strain to kanamycin resistance. The strain is described in EP1155139B1, and the transformation technique in Kirchner et al J Biotechnol. 2003, 104:287-99.

Example 5

L-Valine Formation

The 13032ΔpanBC pEKEx2ATC strain as well as the 13032ΔpanBC PEKEx2 control strain were cultivated in the medium CGIII (Menkel et al 1989, Appl. Environ. Microbiol. 55:684-8) at 30° C. The medium CGIII was inoculated with this at an optical density of 1. The medium CG12 comprises per liter: 20 g $(NH_4)_2SO_4$, 5 g uric acid, 1 g $KH_2PO_4$, 1 g $K_2HPO_4$, 0.25 g $Mg_2O_4.7\ H_2O$, 42 g 3-morpholinopropane-sulfonic acid, 10 mg $CaCl_2$, 10 mg $FeSO_4.7\ H_2O$, 10 mg $MnSO_4.\ H_2O$, 1 mg $ZnSO_4.7\ H_2O$, 0.2 mg $CuSo_4$, 0.02 mg $NiCl_2.6\ H_2O$, 0.2 mg biotin, 40 g glucose, and 0.03 mg protokatechuic acid. The culture was incubated at 30° C. and 170 revolutions per minute, and after 48 hours the L-valine accumulation in the medium was determined with HPLC. This was carried out with o-phthaldialdehyde, as described (Hara et al 1985, Analytica Chimica Acta 172:167-173). The particular L-valine concentrations are shown in table 2.

TABLE 2

| Strain | L-valine |
|---|---|
| 13032ΔpanBC pEKEx2ATC | 11.0 mM |
| 13032ΔpanBC pEKEx2 | 8.1 mM |

---

The invention claimed is:

1. A method for increasing fermentative production of L-valine in a culture medium containing an L-valine-producing Coryneform bacterium, which comprises the step of transforming the L-valine-producing Coryneform bacterium by introducing therein a vector comprising at least one polynucleotide coding for transaminase C having SEQ ID NO: 2 from *Corynebacterium glutamicum* to obtain a recombinant L-valine-producing Coryneform bacterium having increased transaminase C activity over that of the corresponding wild-type L-valine-producing Coryneform bacterium through an increase in transaminase C gene expression, wherein the increased transaminase C gene expression of the transformed L-valine-producing Coryneform bacterium over the corresponding wild-type L-valine-producing Coryneform bacterium results from an exogenous increase in the gene copy count of polynucleotides coding for transaminase C from *Corynebacterium glutamicum*, and also from deactivation of pantothenate synthesis B (panB) and pantothenate synthesis C (panC) genes.

2. The method according to claim 1, wherein a plasmid is used as a vector.

3. The method according to claim 2, wherein at least one component of the vector is a plasmid which is selected from the group consisting of pZ1, pEKEx1, pHS2-1, pHM1519, pBL1, pGA1, pCG4, pNG2, pAG1, and pEkEx2.

4. The method according claim 1, wherein the wild-type L-valine-producing Coryneform bacterium is a Corynebacterium selected from the group consisting of *Corynebacterium glutamicum, Corynebacterium acetoglutamicum, Corynebacterium thermoanimogenesis, Brevibacterium flavum, Brevibacterium lactofermentum*, and *Brevibacterium divaicatum*.

5. The method according to claim 4, wherein the wild-type L-valine-producing Coryneform bacterium is selected from the group consisting of microorganisms Corynebacterium glutamicum ATCC13032,
Corynebacterium acetoglutamicum ATCC15806,
Corynebacterium acetoacidophilum ATCC 13870,
Corynebacterium thermoaminogenes PERM BP-1539,
Brevibacterium flavum ATCC14067,
Brevibacterium lactofermentum ATCC13869, and
Brevibacterium divaricatum ATCC14020.

6. The method according to claim 1, wherein a Coryneform bacterium is used that comprises a Transaminase C gene having SEQ ID NO: 1 from *Corynebacterium glutamicum* with the gene identification number NCgl2510 of the database of the "National Institute of Health".

7. The method according to claim 2 wherein the L-valine-producing Coryneform bacterium is 13032ΔpanBC transformed by introducing as the vector the plasmid pEKEx2ATC.

* * * * *

SEQUENCE LISTING

<160> NUMBER OF SEQ ID NOS: 6

<210> SEQ ID NO 1
<211> LENGTH: 1161
<212> TYPE: DNA
<213> ORGANISM: Corynebacterium glutamicum

<400> SEQUENCE: 1

```
ctatttttg atgaattctc cgattttgcg cacaccttca atggtgtctt cctttgacgc      60
gcacaggctc aaacgaatcc acttgtggcc ttcctcagga tcaaaatcaa cacccggcgc     120
gacggccacg cccgcttcat cgagcaaacg caatgcccat tcctctgaat catcggtgta     180
tgcagaaaca tcgacccaca aatacaggcc gccatccggg tcggcgaaag tgccaagccc     240
gatttcaggg agcttatcga cgaacacctc ccgggcctcg cgatacgctt caacgtgggc     300
atcaagttcg gccccagcct ccaaagtgaa ggctgcgcgt cccgcagcct gcccgatggc     360
aggagcacac aaggaaagag aagcctgcag gttttcaatc ggtgtgacca gctcatctgg     420
aacgatgatc caacccacgc gccaacccgt catggagaag tacttggaca aggtacccac     480
cacgatggcg ttcttggaaa actgatgcgc agttgccagc ggacgaccaa agctcatgcc     540
gtggtagtcc tcatcagaga taagaacagc atcattgtca tcgcaccact ggcgatgcg     600 ctctagctct tccggatcaa tgatggtgcc cgttgggttt cctgggctgg tgacaataac     660
agccttcggc ttgtgtggca gttcctccaa catttgagcg gttggctgga aacgagtctc     720
tgcagtacag cgcaggttca gaaccttcgc ccccaaagat tccagaatat tgcgatatgc     780 cgggtaccc gggtaggca ttgccacata atccccgtga tccaaggtgg cgataaacga     840
tgccacgaat ccacctgaag aaccggtggt gacaataaca ttgtcagggt tggtgtctac     900
gtcataagta gcagagtgcc aatcggcgat gcgttcacgg aactcacgat caccaatcac     960
ctcggtgtat cccaaaggac ccgagcgaag agcgatctct gcttcttcga tgactgcttc    1020
tggcgcacca gttgacggct ggccagcgca gaacattaag gtgtctttgc cttcgcgcct    1080
gcgacggtgg actcggtcca acatctgcat gacgcgaaac ggctgaacat tgcttctagt    1140
gcttggcttc ataagagaca a                                              1161
```

<210> SEQ ID NO 2
<211> LENGTH: 386
<212> TYPE: PRT
<213> ORGANISM: Corynebacterium glutamicum

<400> SEQUENCE: 2

Met Ser Leu Met Lys Pro Ser Thr Arg Ser Asn Val Gln Pro Phe Arg

```
              1               5                  10                 15
        Val Met Gln Met Leu Asp Arg Val His Arg Arg Arg Glu Gly Lys
                         20                  25                  30

Asp Thr Leu Met Phe Cys Ala Gly Gln Pro Ser Thr Gly Ala Pro Glu
                         35                  40                  45

Ala Val Ile Glu Glu Ala Glu Ile Ala Leu Arg Ser Gly Pro Leu Gly
                50                  55                  60

Tyr Thr Glu Val Ile Gly Asp Arg Glu Phe Arg Glu Arg Ile Ala Asp
        65                  70                  75                  80

Trp His Ser Ala Thr Tyr Asp Val Asp Thr Asn Pro Asp Asn Val Ile
                         85                  90                  95

Val Thr Thr Gly Ser Ser Gly Gly Phe Val Ala Ser Phe Ile Ala Thr
                        100                 105                 110

Leu Asp His Gly Asp Tyr Val Ala Met Pro Thr Pro Gly Tyr Pro Ala
                        115                 120                 125

Tyr Arg Asn Ile Leu Glu Ser Leu Gly Ala Lys Val Leu Asn Leu Arg
                        130                 135                 140

Cys Thr Ala Glu Thr Arg Phe Gln Pro Thr Ala Gln Met Leu Glu Glu
        145                 150                 155                 160

Leu Pro His Lys Pro Lys Ala Val Ile Val Thr Ser Pro Gly Asn Pro
                        165                 170                 175

Thr Gly Thr Ile Ile Asp Pro Glu Glu Leu Arg Ile Ala Lys Trp
                        180                 185                 190

Cys Asp Asp Asn Asp Ala Val Leu Ile Ser Asp Glu Asp Tyr His Gly
                        195                 200                 205

Met Ser Phe Gly Arg Pro Leu Ala Thr Ala His Gln Phe Ser Lys Asn
            210                 215                 220

Ala Ile Val Val Gly Thr Leu Ser Lys Tyr Phe Ser Met Thr Gly Trp
        225                 230                 235                 240

Arg Val Gly Trp Ile Ile Val Pro Asp Glu Leu Val Thr Pro Ile Glu
                        245                 250                 255

Asn Leu Gln Ala Ser Leu Ser Leu Cys Ala Pro Ala Ile Gly Gln Ala
                        260                 265                 270

Ala Gly Arg Ala Ala Phe Thr Leu Glu Ala Gly Ala Glu Leu Asp Ala
                        275                 280                 285

His Val Glu Ala Tyr Arg Glu Ala Arg Glu Val Phe Val Asp Lys Leu
                        290                 295                 300

Pro Glu Ile Gly Leu Gly Thr Phe Ala Asp Pro Asp Gly Gly Leu Tyr
        305                 310                 315                 320

Leu Trp Val Asp Val Ser Ala Tyr Thr Asp Asp Ser Glu Glu Trp Ala
                        325                 330                 335

Leu Arg Leu Leu Asp Glu Ala Gly Val Ala Val Ala Pro Gly Val Asp
                        340                 345                 350

Phe Asp Pro Glu Glu Gly His Lys Trp Ile Arg Leu Ser Leu Cys Ala
                        355                 360                 365

Ser Lys Glu Asp Thr Ile Glu Gly Val Arg Lys Ile Gly Glu Phe Ile
        370                 375                 380

Lys Lys
        385

<210> SEQ ID NO 3
        <211> LENGTH: 40
        <212> TYPE: DNA
        <213> ORGANISM: Artificial Sequence
        <220> FEATURE:
```

```
<223> OTHER INFORMATION: Description of Artificial Sequence: Synthetic
      Construct

<400> SEQUENCE: 3
atggtaggtc tcaaatgtct cttatgaagc caagcactag                           40

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 4
atggtaggtc tcagcgcttt ttttgatgaa ttctccgatt ttg                       43

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 5
cgggatccaa ggagatatag atatgtctct tatgaagcca agca                      44

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 6
cgggatccct attttttgat gaattctcc                                       29
```